United States Patent [19]

Seagle et al.

[11] Patent Number: 5,710,510
[45] Date of Patent: Jan. 20, 1998

[54] APPARATUS AND METHOD FOR INTRA PROCESS ON WAFER MONITORING OF DEPOSITED LAYER PERMEABILITY

[75] Inventors: David John Seagle, Morgan Hill; Joseph Francis Smyth, Los Altos, both of Calif.

[73] Assignee: International Business Machines Corporation, Armonk, N.Y.

[21] Appl. No.: 692,685

[22] Filed: Aug. 6, 1996

[51] Int. Cl.$^6$ .................... G01R 33/12; G01N 27/72; G11B 5/127; H01F 7/06
[52] U.S. Cl. .................... 324/210; 324/235; 324/239; 29/603.09
[58] Field of Search ................ 324/210, 235, 324/262, 239, 243; 29/593, 603.01, 603.09

[56] References Cited

U.S. PATENT DOCUMENTS

| | | | |
|---|---|---|---|
| 3,336,154 | 8/1967 | Oberg et al. | 117/93.2 |
| 5,393,557 | 2/1995 | Darling, Jr. | 427/10 |

FOREIGN PATENT DOCUMENTS

| | | |
|---|---|---|
| 5 3001-267 | 1/1978 | Japan. |
| 61-253615 | 11/1986 | Japan. |

*Primary Examiner*—Walter E. Snow
*Attorney, Agent, or Firm*—Baker, Maxham, Jester & Meador

[57] ABSTRACT

A monitoring apparatus is provided for determining permeabilities of a vacuum-deposited second pole piece of a magnetic head at the wafer level by providing wafer-mounted monitors which have layers formed by the same masking and deposition steps employed in making the magnetic heads so that the layers of the monitors are replicated layers, except for a shaping layer on top of a replicated second pole piece of some of the monitors. Each monitor is a transformer wherein each of a primary winding and a secondary winding comprises essentially a replicated magnetic head. The first and second pole pieces of the replicated magnetic heads are joined so as to magnetically couple the primary and secondary windings that constitute the transformer. The replicated shaping layer is omitted in part to expose a portion of one of the replicated second pole pieces of a monitor, such as the front slope, the back slope or the yoke portion of the replicated second pole piece which corresponds to the front slope, the back slope or yoke respectively of the magnetic head. When a current is conducted through the replicated coils of the monitor a voltage reading can be taken to indicate the permeability of the exposed portion of the replicated second pole piece of the monitor.

50 Claims, 9 Drawing Sheets

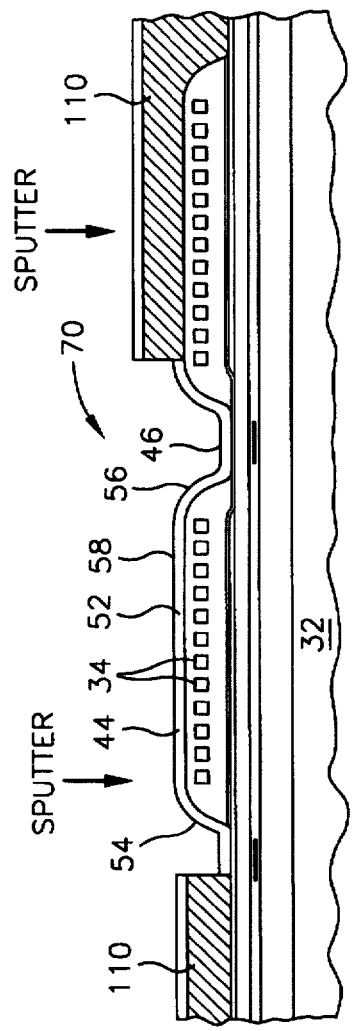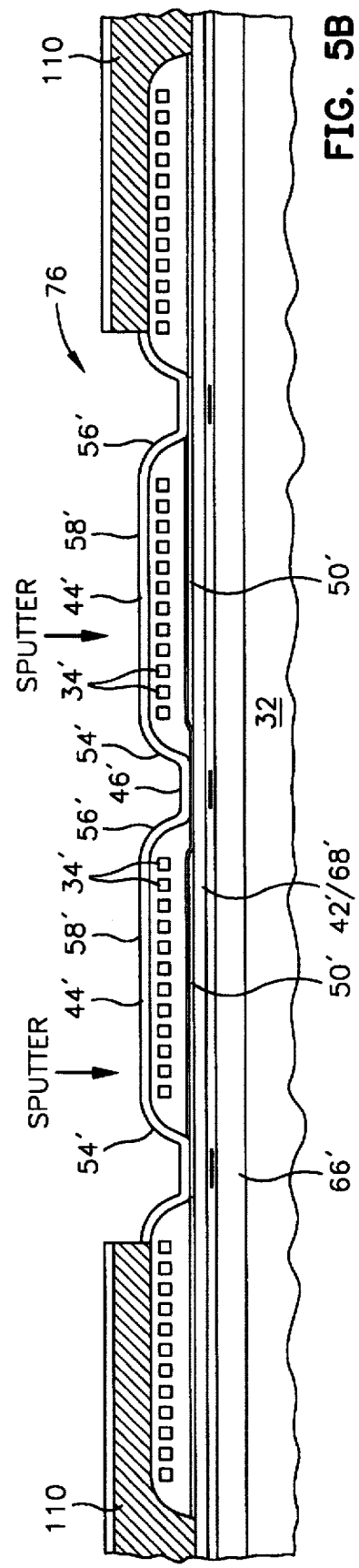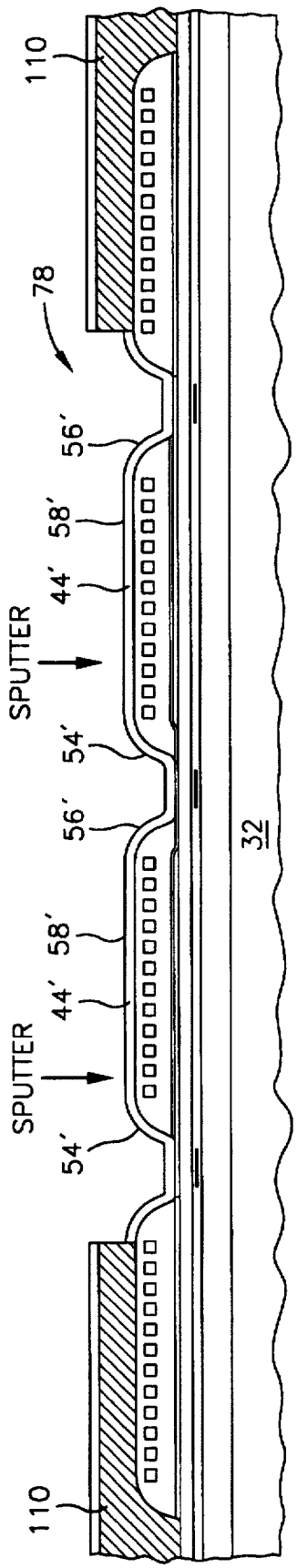

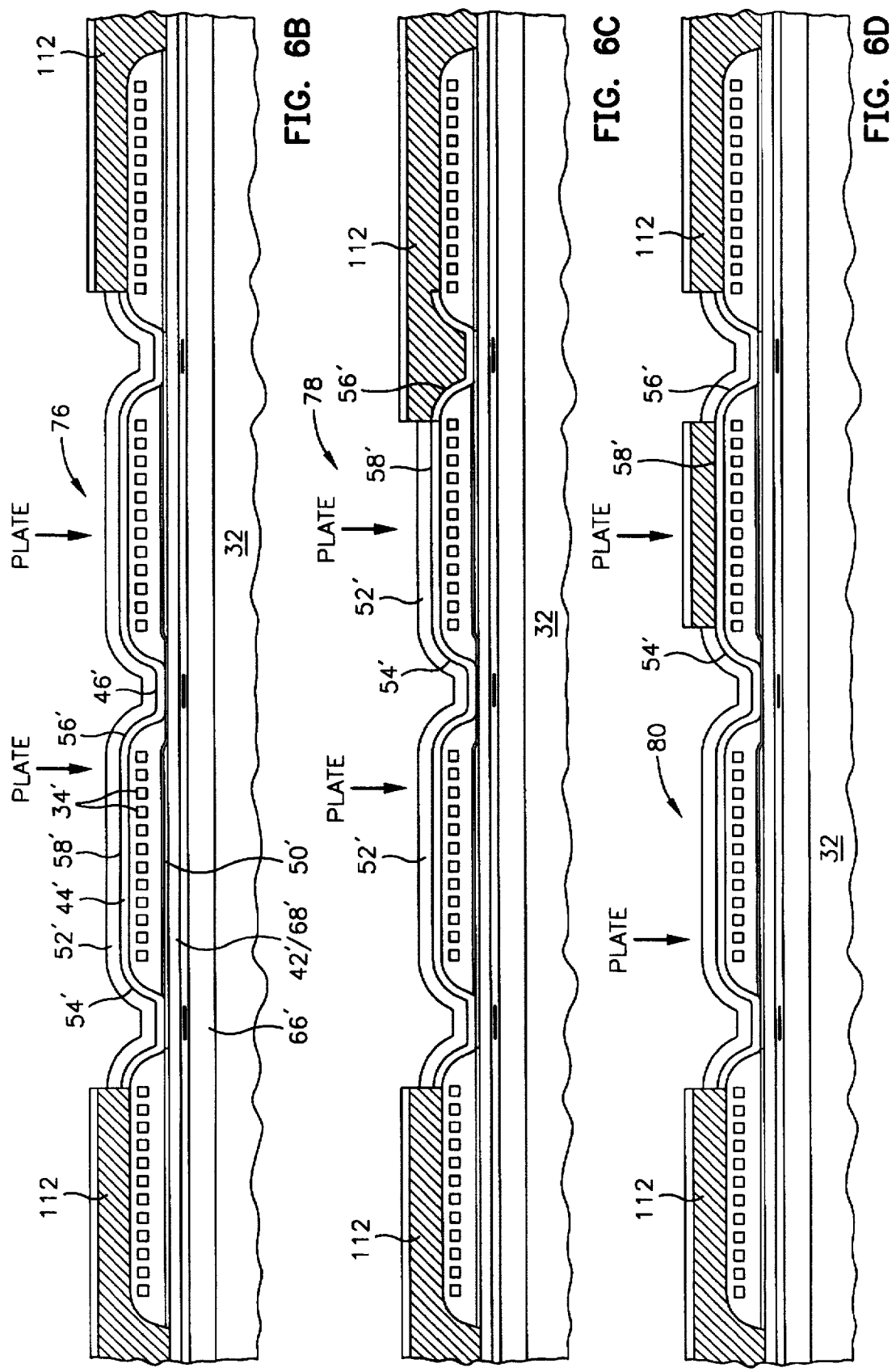

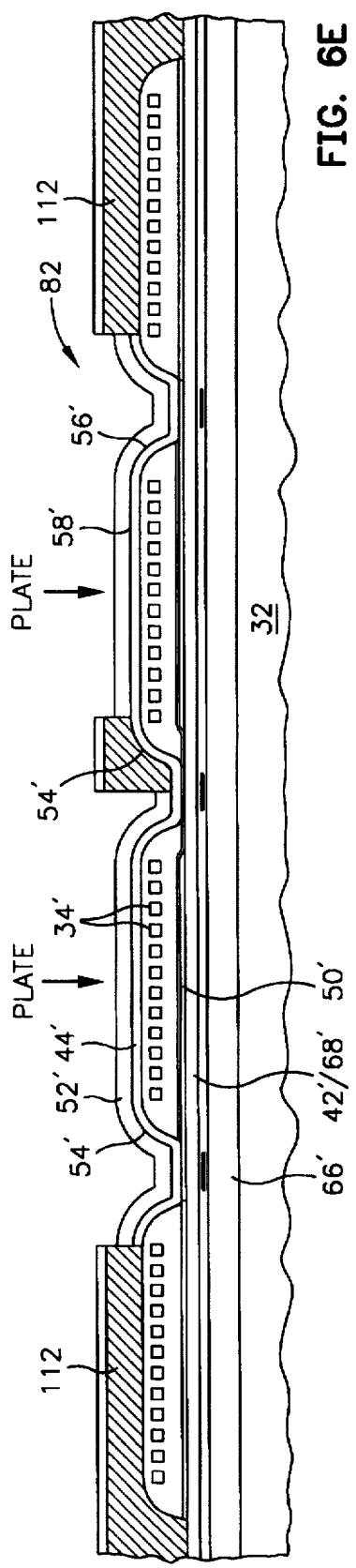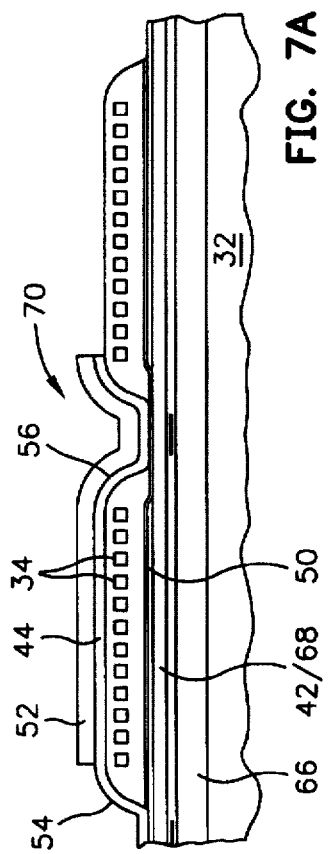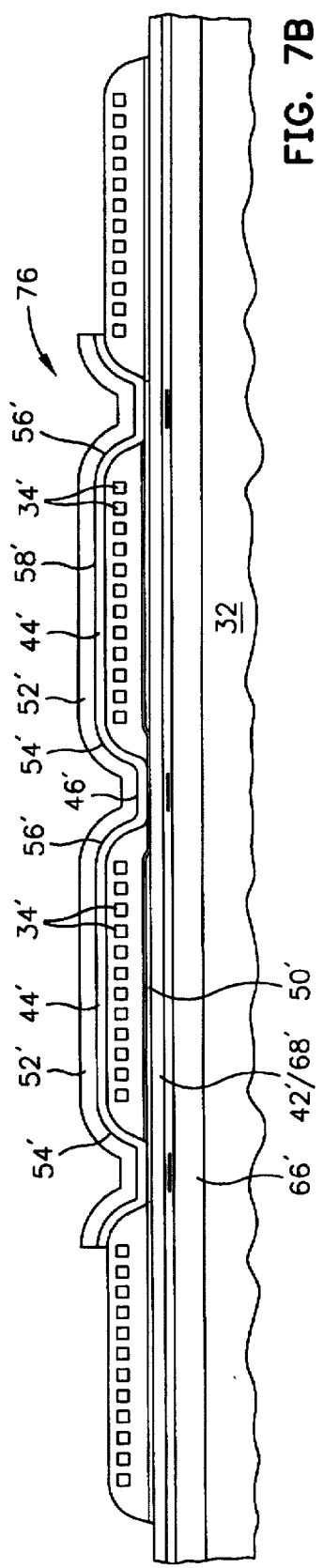

△ CONTROL
□ FRONT SLOPE
◇ BACK SLOPE
○ YOKE (WAFER LEVEL)

APPARATUS AND METHOD FOR INTRA PROCESS ON WAFER MONITORING OF DEPOSITED LAYER PERMEABILITY

BACKGROUND OF THE INVENTION

1. Field of the Invention

The present invention relates to precise monitoring of the magnetic permeability of a thin film when deposited on nonplanar topography, and more particularly to a monitor located on a wafer which will indicate magnetic properties of selected portions of magnetic head pole pieces with the pieces being vacuum-deposited on the wafer.

2. Description of the Related Art

An inductive write head includes one or more coil layers embedded in an insulation stack that is sandwiched between first and second pole pieces. In a merged magnetoresistive (MR) head, an inductive write head is merged with an MR read head that includes an MR sensor sandwiched between a pair of gap layers, that are in turn, sandwiched between a pair of shield layers. In a merged MR head, a single magnetic layer serves both as a shield layer for the MR sensor and as a first pole piece for the write head. In a piggyback MR head, these functions are performed by separate layers. Either a merged MR head or a piggyback MR head is typically employed as a combined head in a magnetic disk or tape drive. The combined head has an air bearing surface (ABS) which is borne on a thin cushion of air (an "air bearing") generated by a moving tape or disk during recording and playback functions.

The second pole piece of the write head portion of a combined head has nonplanar topography due to the presence of an insulation stack. The topography of the second pole piece includes a front slope, a back slope and flat yoke portion therebetween. The front slope extends from the ABS to the yoke and the back slope extends from the yoke to a back gap where the first and second pole pieces are magnetically coupled. It is important that the front and back slopes and the yoke of the second pole piece have good permeability to conduct magnetic flux to and from a disk or tape. Permeability of each of these portions quantifies the ease of magnetization and is determined from the slope of a B/H loop for the particular portion. When the second pole piece is formed by plating, there is generally no problem with permeabilities of the front and back slopes and yoke. However, when the second pole piece is formed by vacuum deposition, such as r.f. sputtering or ion beam sputtering, there can be a problem with the front and/or back slope caused by the relative angle of incidences of the deposition on the various surfaces, as well as by shadowing due to adjacent components. Before and during the manufacture of magnetic heads it is important to know whether the front slope, back slope and yoke portions of a vacuum-deposited second pole piece have sufficient permeability when predetermined manufacturing steps are employed. This should be known at the wafer level before dicing the wafer into rows of sliders in order to avoid incurring the time and cost of further processing.

Edges of the first and second pole piece layers in the write head and edges of the layers in the MR read head form a portion of the ABS which are subject to wear and corrosion. Consequently, structures and materials used for the second pole piece must bestow good wear and corrosion properties. One solution is embodied in a multilayer structure that incorporates FeN/NiFeN. The layers are typically vacuum-deposited, as by sputtering. While these layers are desirable from the standpoint of wear and corrosion, they exhibit low permeability because of vacuum deposition at the wafer level. To overcome this problem, a magnetic shaping layer, such as Permalloy ($Ni_{80}Fe_{21}$) which has a higher permeability than the FeN/NiFeN layers, is plated on top of the second pole piece to increase its permeability. The shaping layer typically covers only the back slope and the yoke since its extension to the ABS limits linear bit density of the write head and may increase susceptibility of the head to corrosion and wear. In another embodiment the shaping layer also covers the front slope. In both embodiments it is important that each of the back slope portion and the yoke portion of the second pole piece contribute to permeability, in spite of the presence of a shaping layer. The pole portion of the front gap slope region must carry all the flux in the absence of a shaping layer but even the back slope with a shaping layer is a problem. Since the amount of flux conducted by the yoke is largest at the backgap, the shaping layer can magnetically saturate limiting available flux to the front. This can only be alleviated by reasonable permeability in the pole. In the first embodiment the front slope is of particular concern since it does not have a shaping layer. Accordingly, before and during manufacturing of a magnetic head the ability to monitor the permeability of the front slope, back slope and yoke of the second pole piece would yield an important indication of the prospect for acceptable write head operation. Generally, since the shaping layer is plated, it does not need monitoring since it is virtually assured of providing its designed permeability.

Various schemes have been employed at the wafer level to determine the permeability of vacuum-deposited second pole pieces before additional work is completed. One scheme places monitors in the deposition tool adjacent the wafers for collecting thin film samples of the deposited layers including the second pole piece. These monitors are then removed to be tested for permeability. However, these monitors are flat samples and do not indicate the loss in permeability of one or more layers vacuum-deposited on a slope, such as the front slope and back slope of a second pole piece. Another scheme injects alternating current into write coil pads at the wafer level and then measures the inductance of the write head. This measurement indicates the overall efficiency of the write head but does not indicate the second pole piece parameter values. In a further scheme a coil turn is placed at the ABS of a write head at the wafer level to form a transformer in which the coil of the head is a primary and the coil turn is a secondary. Current is introduced into the primary and a reading is taken at the secondary to determine permeability. Again this measures the overall efficiency of the write head and is non-specific with respect to magnetic characteristics of the second pole piece. Therefore, there is a strong-felt but yet unsatisfied need to measure the permeabilities of the front slope the back slope and the yoke of a vacuum-deposited second pole piece at the wafer level in order to evaluate the quality of the deposition process before additional expense occurs after the wafer level.

SUMMARY OF THE INVENTION

The present invention provides a wafer-mounted monitor for checking the permeability of a selected portion of the second pole piece of a magnetic write head while the piece is being fabricated on the wafer. Additional monitors can be added to check the permeability of other selected portions of the second pole piece. If the front slope, back slope and yoke portions are to be checked three monitors would be employed. Each monitor includes a primary winding and a secondary winding of a transformer. Each of the primary and the secondary windings are replicas of the write heads and are formed on the wafer simultaneously with the write heads. The deposition steps which form the elements of the write heads simultaneously form replicas of all of these elements for each of the monitors, with an exception. The exception is that the second pole piece shaping layer is omitted from a portion of the second pole piece replica in the primary or secondary of the monitor which corresponds to the selected portion of a magnetic head which is to be checked. Accordingly, if the back slope of the second pole piece of a magnetic head is to be checked, the shaping layer in the monitor is omitted from the back slope of one of the replicated second pole pieces of the monitor.

It is emphasized that the monitors are fabricated simultaneously with the magnetic heads on the same wafer, using the same masking and deposition steps as are used to make the magnetic heads. Further, when this description refers to a magnetic head on a wafer, reference is to one of the many identical magnetic heads which are fabricated on a wafer during production.

Expected permeabilities of selected portions of a second pole piece can be determined by checking a good head without a shaping layer in the selected portions, or by modelling. Accordingly, if the measured permeability of a back slope without a shaping layer in a replicated second pole piece of a monitor does not meet a certain permeability level, it is determined that the back slope deposition is faulty and that corrective measures should be taken. Monitors for the front slope and the yoke operate in the same manner. Each of the windings of a monitor are provided with a pair of pads so that a current can be introduced into the primary winding and a voltage measurement can be taken at the secondary winding (or vice versa) to determine the permeability of the selected portion of a monitored second pole piece. Accordingly, the present invention allows the determination of permeabilities of selected portions of the second pole piece of a magnetic head at the wafer level. If a problem is found, corrective measures can be taken by making adjustments to the vacuum-deposition process, or by adding additional shaping layer material. This is done early in the manufacturing process, thereby potentially saving the time and costs that would otherwise be invested in manufacturing heads certain to be rejected. It should be understood that the invention is not confined to monitoring a vacuum-deposited second pole piece but can be employed for monitoring any magnetic property of any magnetic layer deposited on a wafer.

An object of the present invention is to provide a wafer mounted monitor for monitoring a magnetic property of a magnetic layer deposited on the wafer.

Another object is to provide a wafer mounted monitor for monitoring the permeability of a selected portion of a vacuum-deposited second pole piece of a magnetic head on the wafer.

A further object is to provide a wafer mounted monitor for monitoring the permeability of the front slope or the back slope of a vacuum-deposited second pole piece of a magnetic head on the wafer.

Still another object is to provide a plurality of wafer mounted monitors for monitoring the permeabilities of a plurality of selected portions of a vacuum-deposited second pole piece of a magnetic head on the wafer.

Still a further object is to provide a plurality of wafer mounted monitors for monitoring the permeabilities of a plurality of selected portions of a vacuum-deposited second pole piece of a magnetic head on the wafer without adding any additional masking and/or deposition steps in a process of making a plurality of the magnetic heads on said wafer.

Other objects and advantages of the invention will become apparent upon reading the following description taken together with the accompanying drawings.

BRIEF DESCRIPTION OF THE DRAWINGS

FIG. 5A shows the write head of FIG. 2 just after the formation of the second pole piece by vacuum deposition on a wafer, and FIGS. 5B-5E show vacuum deposition of replicated second pole pieces by the same vacuum deposition step on the same wafer for constructing monitors of the present invention.

FIGS. 6A-6E are similar to FIGS. 5A-5E except a process step is shown for plating a shaping layer on top of the second pole piece of the magnetic head in FIG. 6A and the replicated second pole pieces in FIGS. 6B-6E with portions of the shaping layer omitted from portions of the replicated second pole pieces in FIGS. 6C-6E which correspond to selected portions of the second pole piece of the magnetic head in FIG. 6A.

FIGS. 7A-7E are similar to FIGS. 6A-6E except the magnetic head in FIG. 7A and the monitors in FIGS. 7B-7E are now complete after removal of photoresist layers in FIGS. 6A-6E.

DESCRIPTION OF THE PREFERRED EMBODIMENTS

Figure 1:
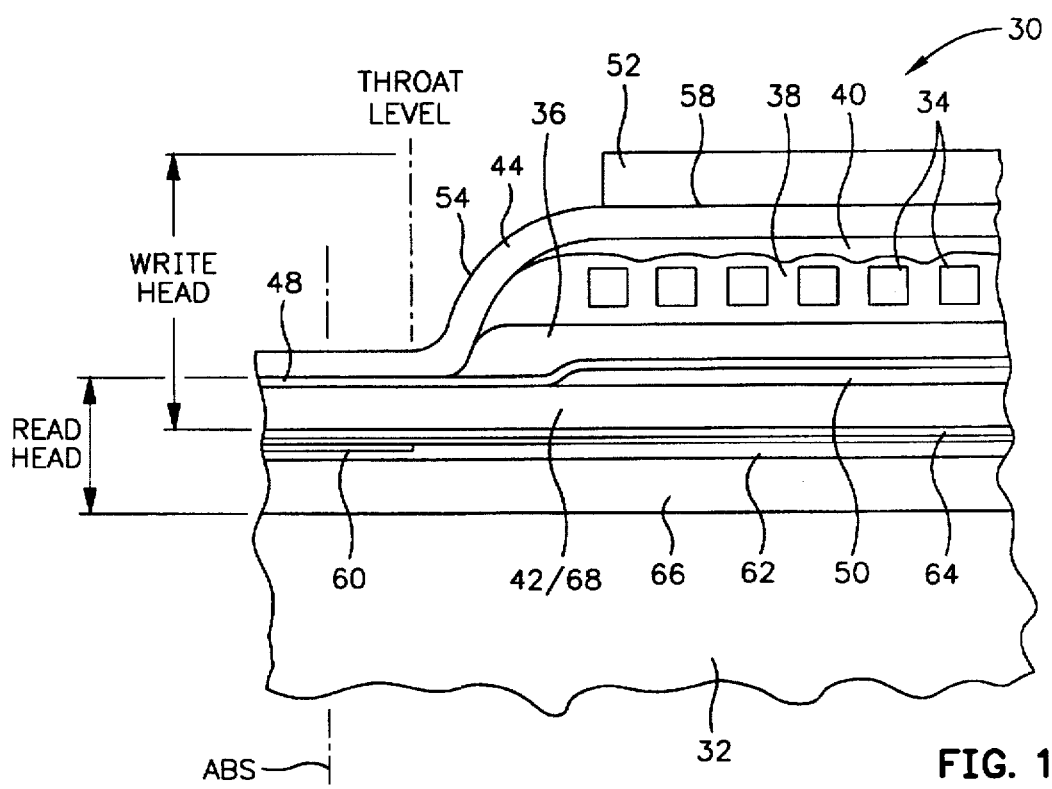
FIG. 1 is a cross-sectional elevational view of a front portion of an exemplary combined magnetic head on a wafer with portions cut away.
Figure 2:
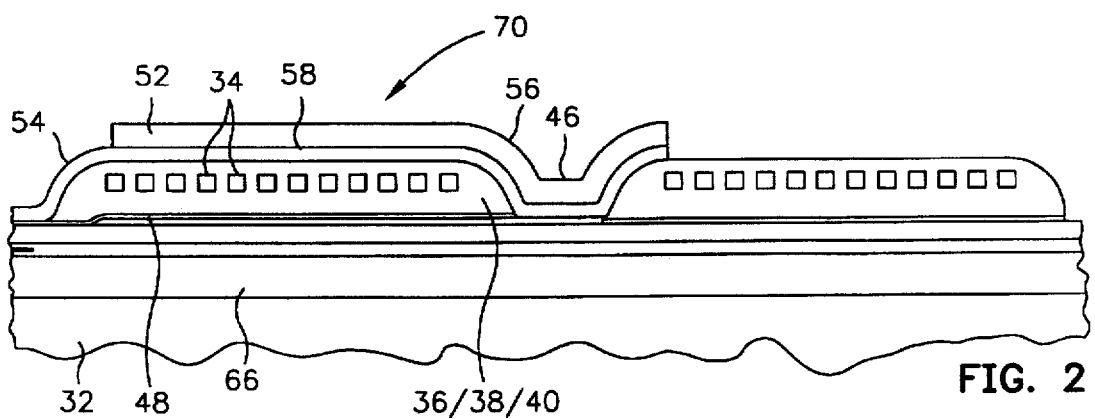
FIG. 2 is a cross-sectional elevational view of front and back portions of the write head portion shown in FIG. 1.

FIG. 1 shows a side view of the from portion of a combined magnetic head 30 which has a read head portion and a write head portion on a wafer substrate 32. The combined head 30 is employed for recording and playback of signals on a magnetic tape on a disk (not shown). The write head portion includes a coil layer 34 embedded in a plurality of insulation layers 36, 38 and 40, the insulation layers forming an insulation stack. The insulation stack is sandwiched between first and second pole pieces 42 and 44, the pole pieces being magnetically coupled at a back gap 46 as shown in FIG. 2 and separated by a gap layer 48 at an air bearing surface (ABS). Generally, a plurality of such heads are formed on a wafer. Each of the first and second pole pieces 42 and 44 may be a multi-layer construction of FeN/NiFeN which resists wear and corrosion at the ABS. After fabrication, the wafer is diced into individual heads.

While the pole piece layers have excellent corrosion qualities they exhibit low permeability, which is compensated for by shaping layers 50 and 52. The shaping layer 50 is sandwiched between the first pole piece 42 and the gap layer 48, and the shaping layer 52 is disposed on top of the second pole piece 44. The shaping layers are composed of a material with high magnetic permeability, such as Permalloy ($Ni_{89}Fe_{21}$). It is necessary that the each pole/shaping layer has sufficient combined moment to place the saturation of the magnetic circuit at a value above that required for the gap fields to saturate the media.

In a typical head fabrication process, the layers of the first and second pole pieces 42 and 44 are vacuum-deposited by sputtering or ion beam deposition. Vacuum depositions on the slopes 54 and 56 have a different micro-structure than the deposition on the yoke portion 58 of the second pole piece. This often produces front and back slopes with low permeabilities. The slopes are also subjected to shadowing from adjacent components which additionally affects their microstructures. Since the yoke 58 of the first pole piece 42 is flat these problems are not normally encountered. However, other manufacturing artifacts and certain operational factors make it desirable to check the permeability of the yoke at the wafer level.

The read head portion of the combined head 30 includes an MR sensor 60 which is sandwiched between first and second gap layers 62 and 64. The gap layers are sandwiched between first and second shield layers 66 and 68. If the combined head 30 is a merged MR head the layer 42/68 is a single layer serving as a second shield for the read head and as a first pole piece for the write head. In another embodiment a double layer separated by a dielectric layer is substituted for the layer 42/68 wherein one layer serves as a second shield for the read head and the other layer serves as a first pole piece for the write head. This latter embodiment is referred to as a "piggyback" MR head.

In the past there has been no scheme for accurately monitoring the permeabilities of selected portions of the second pole piece 58 of the write head. As discussed hereinabove the prior art methods either measured the permeability of a flat layer deposited on a test coupon on the wafer or employed various methods for checking the overall inductance of the write head which grossly corresponds to the compound permeability of the entire head. Since the second pole piece 58 is the primary cause of degraded permeability, there is a strong-felt need for checking selected locations of the second pole piece where permeability problems may occur. By detecting these problems early in the fabrication process changes can be made in the process steps and/or materials to correct the permeability problem. It is highly desirable that this check be made before a wafer is sliced into individual units for processing and assembly.

Figure 3:
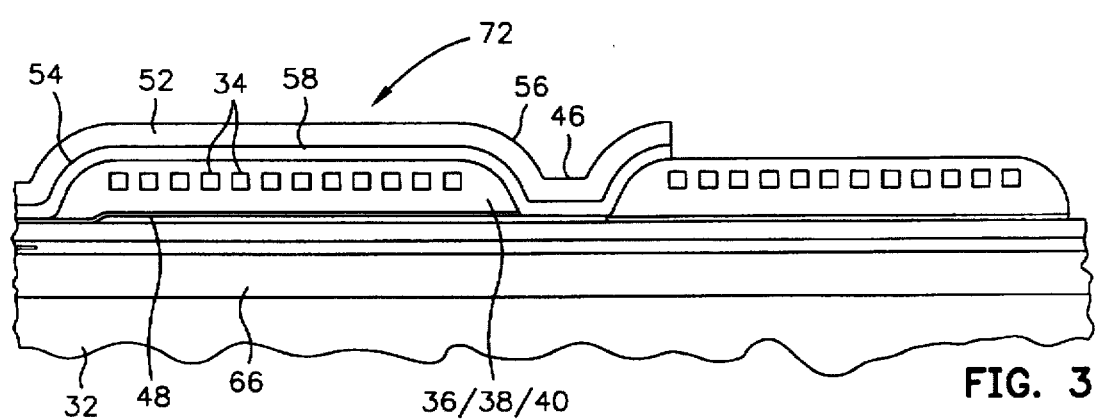
FIG. 3 is the same as FIG. 2 except a shaping layer covers a front slope of the write head.

FIGS. 2 and 3 show two embodiments 70 and 72 respectively of the magnetic heads at the wafer level with a shaping layer 52. FIG. 2 illustrates a more common embodiment wherein the shaping layer does not extend to the ABS. In FIG. 3 the shaping layer extends to the ABS. The embodiment shown in FIG. 2 will be employed in the remainder of this description with the understanding that the described means and methods for monitoring can be applied to the embodiment of FIG. 3.

Figure 4:
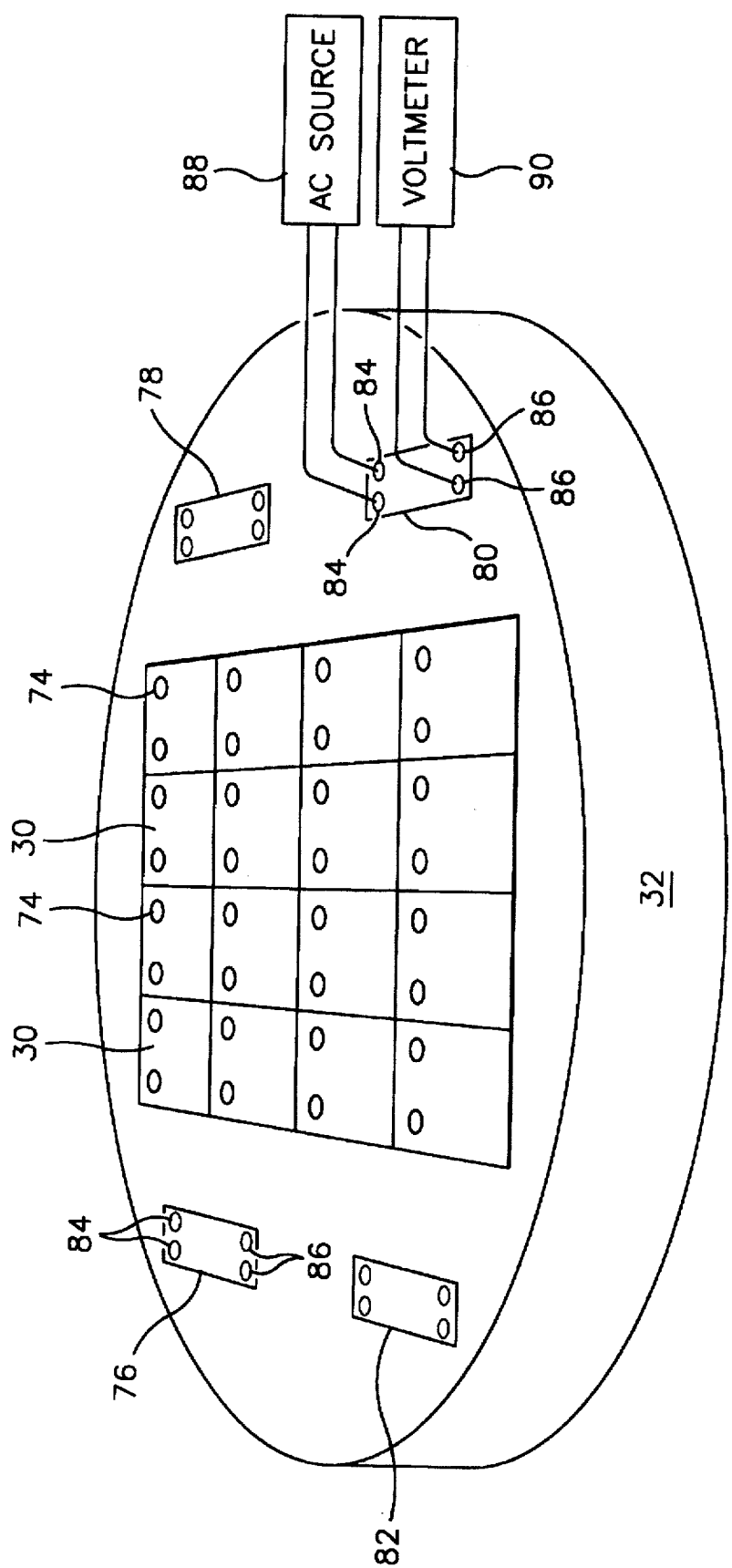
FIG. 4 is a schematic isometric illustration of a plurality of wafer-mounted magnetic heads and a plurality of wafer-mounted monitors according to the present invention for monitoring permeabilities of selected portions of a second pole piece of one of the magnetic heads.
Figure 5D:
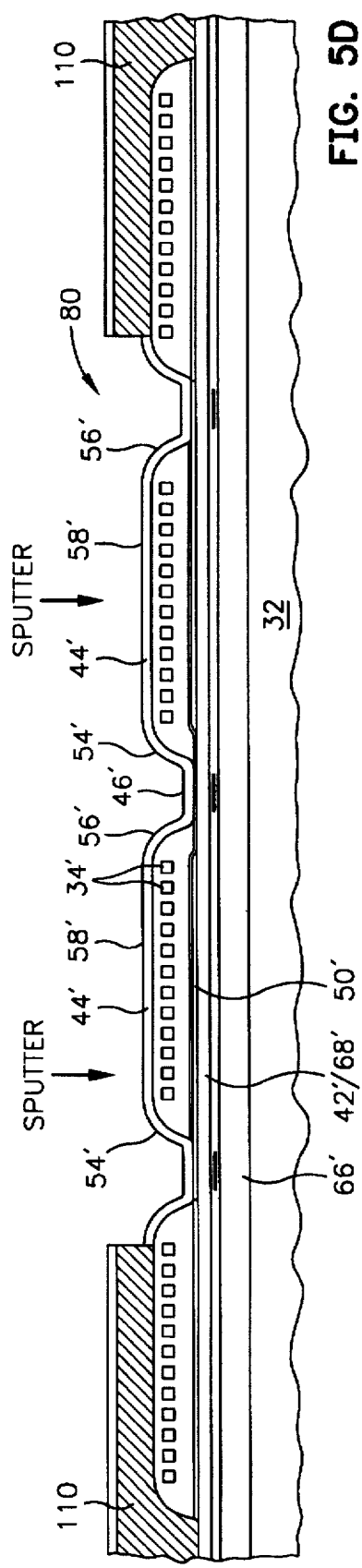
Figure 5E:
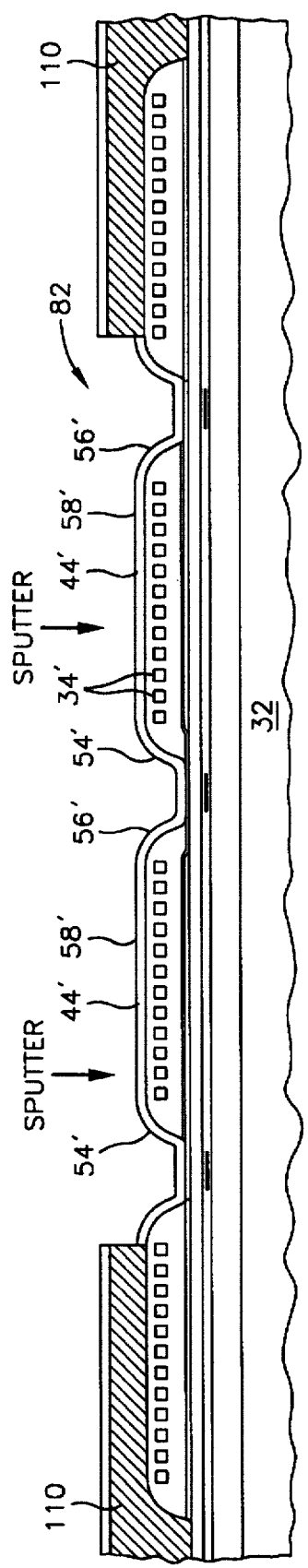
Figure 6A:
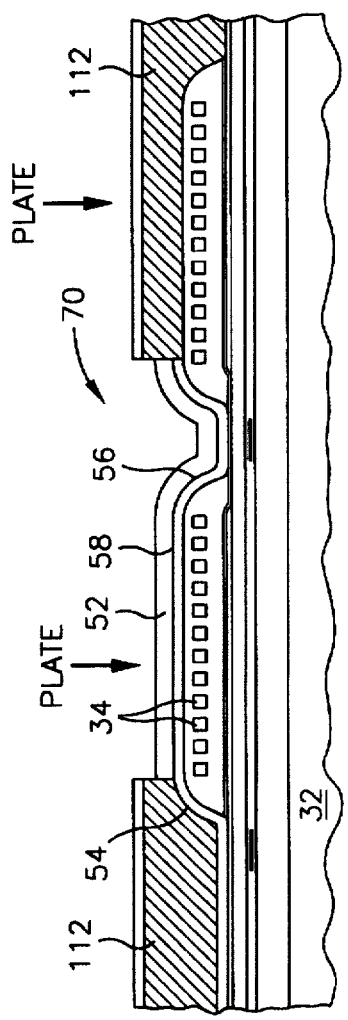

In FIG. 4 there is shown the wafer 32 with a plurality of combined heads 30, each head being shown with a pair of pads 74 which connect to opposite ends of the coil layer 34 shown in FIG. 1. Also on the wafer are monitors 76, 78, 80 and 82, each monitor having a pair of input pads 84 and a pair of output pads 86. FIG. 4 also shows an alternating current source 88 connected to the input pads 84 and a RMS voltmeter or other voltage sensing device 90 connected to the output pads 86 of one monitor for checking the permeability of a selected portion of second pole pieces of the magnetic heads 30. It is important to note that the same steps for forming the layers of the magnetic heads 30 are employed for simultaneously making the monitors 76, 78, 80 and 82 of the present invention. Accordingly, the monitors are made without any additional masking and/or deposition steps and assures measurements on the same depositions as the head. With this arrangement the permeabilities of selected portions of the second pole pieces of the magnetic heads 30 can be checked at the wafer level. This may be done early in fabrication, before assembly, and may be executed on an every wafer basis or audit basis after the fabrication has commenced.

Figure 9:
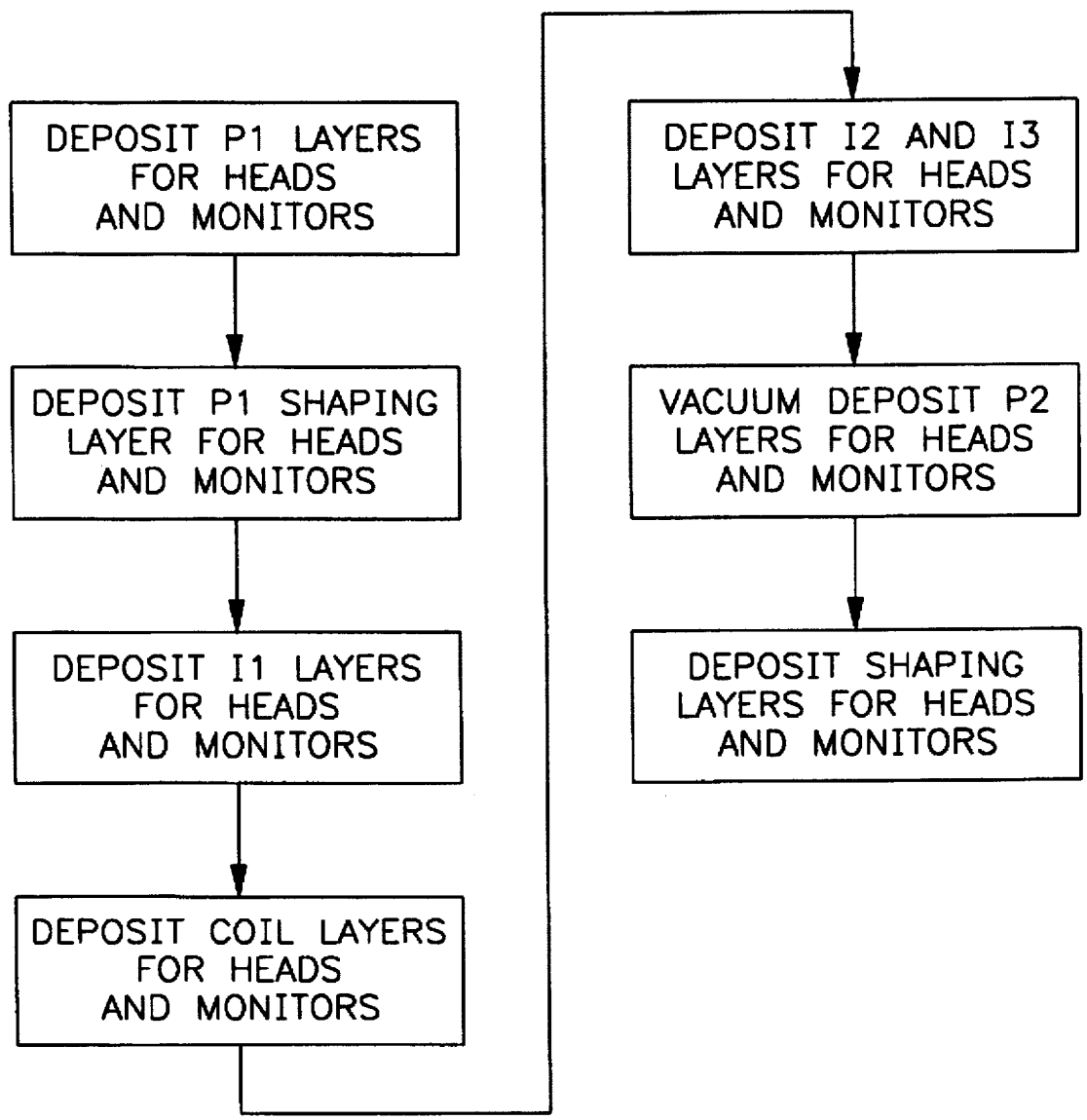
FIG. 9 is a block diagram of processing steps for making the heads and monitors of the present invention.

FIGS. 5A–5E and FIGS. 6A–6E show process steps in making the magnetic head 70 and the monitors 76, 78, 80 and 82 in FIGS. 7A, 7B, 7C, 7D and 7E respectively. FIGS. 5A–5E and FIGS. 6A–6E show intermediate steps in the fabrication of one of the magnetic heads and the monitors. In FIGS. 5A–5E resist layers 110 are employed for the placement of the second pole piece 44 of the magnetic head 70 and the replicated second pole pieces 44' of the monitors 76, 78, 80 and 82 by vacuum deposition, such as sputtering, on a common wafer 32. In FIGS. 6A–6E resist layers 112 are employed for depositing the shaping layer 52 of the magnetic head 70, a replicated shaping layer 52' in FIG. 7E and substantially replicated shaping layers 52' in FIGS. 6B, 6C and 6D by a common plating process on the common wafer 32. The process steps for forming the layers of the magnetic head and the replicated layers of the monitors are shown in FIG. 9.

Figure 7C:
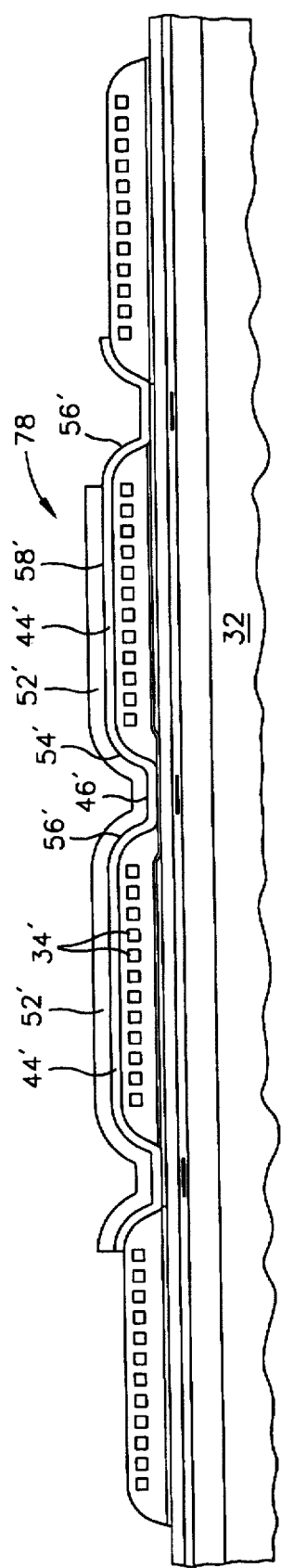
Figure 8:
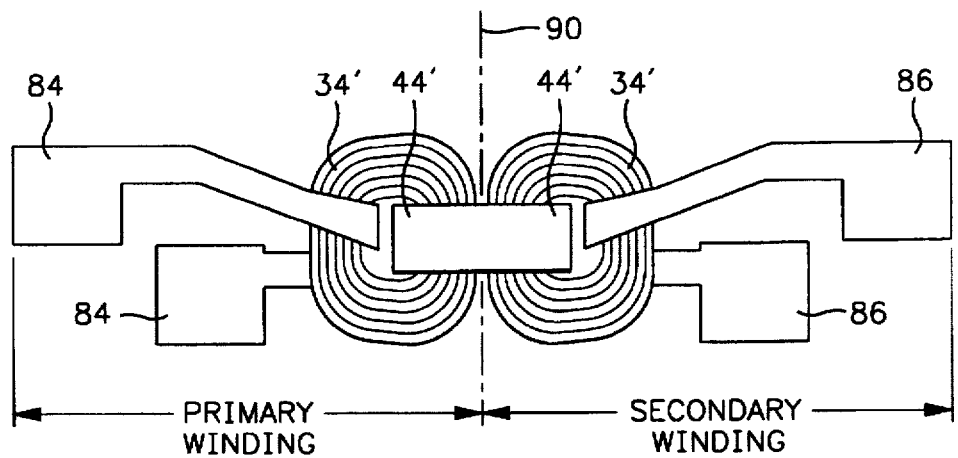
FIG. 8 is a top plan schematic illustration of one of the monitors of the present invention.

The process monitors 76, 78, 80 and 82 have a common configuration which is schematically shown in plan in FIG. 8. Each monitor is essentially a transformer which has a primary winding and a secondary winding wherein each of the primary and secondary windings are made up of layers which are replicated layers of the write heads 70. Since all of the layers of a write head are replicated in a monitor (except the top shaping layer in some instances) the replicated layers are given a prime designation. Accordingly, as shown in FIG. 8 and FIG. 7C, for example, each of the primary and secondary windings of the transformer includes a replicated coil layer 34' which is embedded in a replicated insulation stack which, in turn, is sandwiched between first and second replicated pole pieces 42' and 44'. Each of the replicated pole pieces has replicated shaping layers 50' and 52', with portions of the shaping layers not being replicated, as explained hereinbelow. In order to form the transformer, the replicated second pole pieces 44' are connected at 90, as shown in FIG. 8, to provide an inductive coupling between the primary winding and the secondary winding.

Figure 7D:
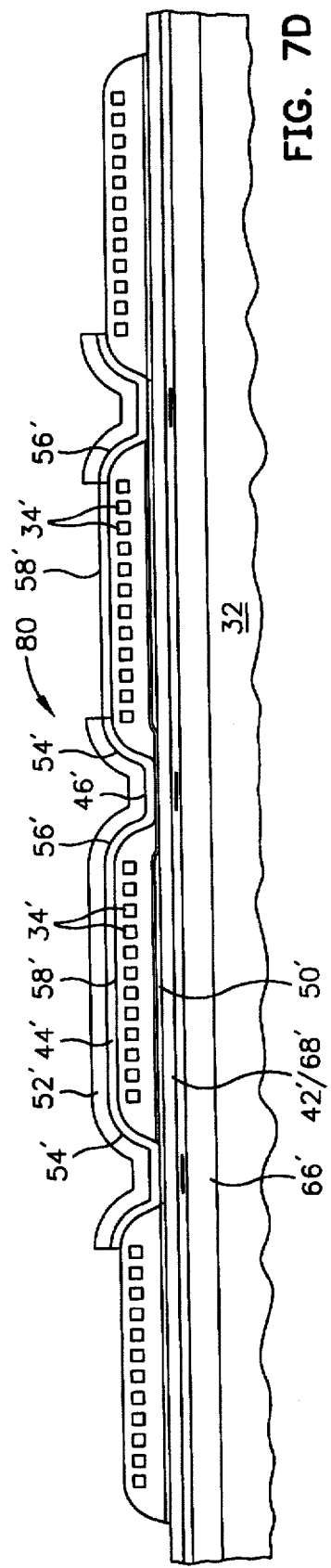
Figure 7E:
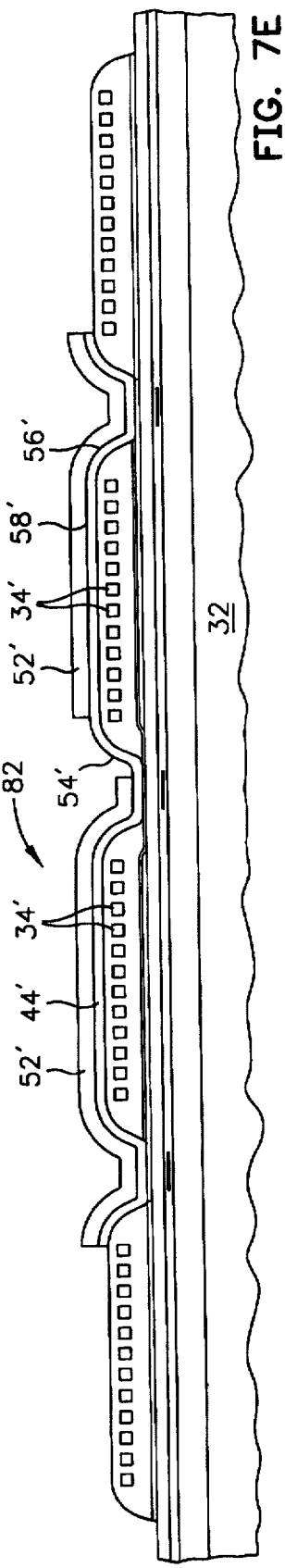

The monitor shown in FIG. 7B is a control monitor having a shaping layer 52' that completely covers the replicated second pole piece portions 44'. This monitor is simply employed for checking the permeability of the replicated shaping layer 52'. Since the shaping layer is virtually assured of sufficient permeability, this monitor may be omitted in a practical embodiment. Each of the monitors 7C, 7D and 7E are employed for checking the permeability of a selected portion of the second pole piece of the magnetic head. This is accomplished by omitting the shaping layer on a portion of the replicated second pole pieces 44' which corresponds to a selected portion of the second pole piece of the magnetic head which is to be tested. Accordingly, in FIG. 7C, the replicated shaping layer 52' is omitted from the replicated back slope 56' so as to check the permeability of the back slope 56 of the magnetic head in FIG. 7A. In FIG. 7D the replicated shaping layer 52' is omitted from the replicated yoke portion 58' of the replicated second pole piece 44' so as to indicate the permeability of the yoke portion 58 of the second pole piece 44 of the magnetic head 70 in FIG. 7A. In the same manner in FIG. 7E, the replicated shaping layer 52' is omitted from the replicated front slope 54' of the replicated second pole piece 44' to indicate the permeability of the front slope 54 of the second pole piece 44 of the magnetic head 70 in FIG. 7A.

Figure 10:
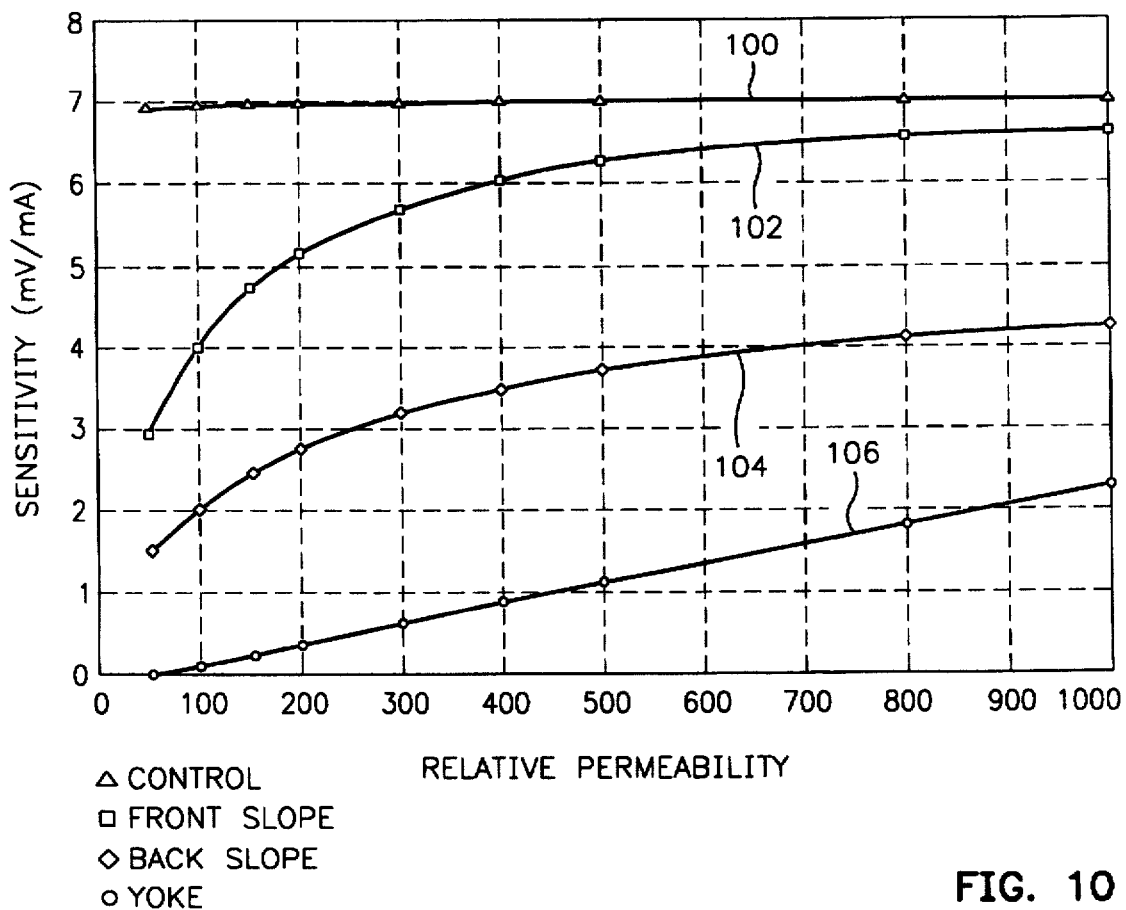
FIG. 10 is a graph from simple electrostatic modelling which shows the sensitivity of the transformers secondary voltage to the current on the primary.

Since the permeabilities are high where the shaping layer is located, the permeabilities at the regions where the replicated shaping layers are omitted can be easily checked to determine whether the exposed portion of the replicated second pole piece 44' meets a standard of permeability. A standard can be derived from known heads or by modelling. Permeability standards for the monitors 76, 78, 80 and 82 are shown by the curves 100, 102, 104 and 106 respectively in FIG. 10. FIG. 10 is a graph from simple electrostatic modelling which shows the sensitivity of the transformers secondary voltage to the current on the primary. This sensitivity is shown as a function of the permeability of the region (frontgap, backgap, yoke) that is under test. The modelling shows high sensitivity to permeability over the range of permeabilities of interest. Experimental sensitivity measurements from the transformers in FIG. 7C–7E can be compared to this modelling to determine the actual permeability of the various regions of the pole. The sensitivity of a monitor may be measured by employing the AC device 88 and the RMS voltage device 90 in FIG. 4, the device 88 being an input device and the device 90 being an output device. A ratio of input to output provides an indication of sensitivity which is shown along the ordinate in FIG. 10. For example, assume that the permeability standard of the back slope 56 of the magnetic head 70 is 300. If the monitor 78 in FIG. 7C shows that the sensitivity is 2.5 this will indicate that there is a problem with the permeability of the back slope 56. The same type of check can be made for the front slope 54' and the yoke 58 by the monitors 82 and 80 respectively by referring to the curves 102 and 106. These checks can be made at the wafer level.

Clearly, other embodiments and modifications of this invention will occur readily to those of ordinary skill in the art in view of these teachings. Therefore, this invention is to be limited only by the following claims, which include all such embodiments and modifications when viewed in conjunction with the above specification and accompanying drawings.

We claim:

1. An apparatus for determining a magnetic property of at least one magnetic head at a wafer level, comprising:

first, second and third substantially identical magnetic heads mounted on a wafer;

each magnetic head having a coil layer and a second pole piece;

the second pole pieces of the second and third magnetic heads being magnetically joined so that the coil layers of the second and third magnetic head are magnetically coupled; and a magnetic shaping layer disposed on the second pole pieces of the second and third magnetic heads except for an exposed portion of the second pole piece of one of the second and third magnetic heads, the exposed portion corresponding to a selected portion of the second pole piece of the first magnetic head.

2. An apparatus as claimed in claim 1, including:

the second pole piece of each of the first, second and third magnetic heads having a front slope, a back slope and a yoke therebetween; and one of the front slope, back slope and the yoke of the second pole piece of one of the second and third magnetic heads being exposed and corresponding to one of the front slope, back slope and the yoke of the second pole piece of the first magnetic head.

3. An apparatus as claimed in claim 2, including:

a monitoring system which includes said second and third magnetic heads and the magnetic shaping layer;

said monitoring system being replicated to provide a plurality of monitoring systems on said wafer; and the shaping layer in each of the monitoring systems exposing a different portion of one of the second pole pieces of the monitoring system which corresponds to a selected portion of the second pole piece of the first magnetic head.

4. An apparatus as claimed in claim 2, including:

a monitoring system which includes said second and third magnetic heads and the magnetic shaping layer;

said monitoring system being replicated to provide a plurality of monitoring systems on said wafer; and a front slope of one of the second pole pieces of a first one of the monitoring systems being exposed by a magnetic shaping layer;

a back slope of one of the second pole pieces of a second one of the monitoring systems being exposed by a magnetic shaping layer; and a yoke of one of the second pole pieces of a third one of the monitoring systems being exposed by a magnetic shaping layer.

5. An apparatus as claimed in claim 4, further including:

a current source coupled to the first coil layer; and means for receiving from the second coil layer an output indicative of a magnetic property of said selected portion.

6. An apparatus as claimed in claim 5, wherein said magnetic property is permeability.

7. An apparatus for determining a magnetic property of magnetic structures on a wafer, comprising:

a wafer;

a plurality of substantially identical magnetic heads fabricated on the wafer;

a first one of the magnetic heads having at least one coil layer embedded in an insulation stack and the insulation stack being sandwiched between first and second pole pieces;

a monitoring system for monitoring a magnetic property of a selected portion of the second pole piece of said first magnetic head including:

first and second replicated magnetic heads wherein each replicated magnetic head replicates said first magnetic head and wherein the first and second replicated magnetic heads have first and second replicated coil layers respectively and first and second replicated second pole pieces respectively;

means for inductively coupling the first and second replicated magnetic heads;

a magnetic shaping layer covering each of the first and second replicated second pole pieces except for an exposed portion which corresponds to a selected portion of said second pole piece of said first magnetic head; and the first replicated coil layer having first and second ends for conducting a current through the first replicated coil; and the second replicated coil layer having first and second ends for providing an output representing said magnetic property of said selected portion of the second pole piece of said first magnetic heads.

8. An apparatus as claimed in claim 7, wherein said magnetic property is permeability.

9. An apparatus as claimed in claim 8, wherein the second pole piece and the first and second replicated second pole pieces are deposited by sputtering.

10. An apparatus as claimed in claim 9, including:

a plurality of monitoring systems on said wafer;

one of the first and second replicated second pole pieces of each of at least some of the monitoring systems having a different exposed portion which corresponds to a respective selected portion of said second pole piece of said first magnetic head.

11. An apparatus as claimed in claim 10, including:

each of the second pole piece and the first and second replicated second pole pieces having front and back slopes with a yoke portion therebetween.

12. An apparatus as claimed in claim 11, wherein at least one of said selected portions is the back slope of the second pole piece.

13. An apparatus as claimed in claim 11, wherein at least one of said selected portions is the front slope of the second pole piece.

14. An apparatus as claimed in claim 11, wherein at least one of said selected portions is the yoke of the second pole piece.

15. An apparatus as claimed in claim 11, including:

a plurality of selected portions including the front and back slopes and the yoke of the second pole piece; and one of the first and second replicated second pole pieces of each of the monitoring systems having an exposed portion which corresponds to a respective selected portion of said second pole piece.

16. An apparatus as claimed in claim 15, including:

one of the monitoring systems having its first and second replicated second pole pieces completely covered by a shaping layer.

17. An apparatus as claimed in claim 15, including:

means connected to the first and second ends of the first replicated coil layer for introducing said current into said first replicated coil layer and means connected to the first and second ends of the second replicated coil layer for receiving an output from the second replicated coil layer.

18. An apparatus as claimed in claim 15, including:

a magnetic shaping layer on top of only said back slope and said yoke of said second pole piece of said first magnetic head.

19. An apparatus as claimed in claim 15, including:

a magnetic shaping layer on top of the front and back slopes and the yoke of said second pole piece of said first magnetic head.

20. A combination of a monitored magnetic layer and a monitoring system for monitoring a magnetic property of at least one selected portion of said monitored magnetic layer, comprising:

a wafer;

a monitored magnetic layer deposited on said wafer by a deposition A;

at least one monitoring system on said wafer, including:

first and second monitoring coils deposited on the wafer by a deposition B;

a monitoring magnetic layer deposited over the first and second monitoring coils respectively by said deposition A, the monitoring magnetic layer substantially replicating said monitored magnetic layer over each of the first and second monitoring coil layers, the monitoring magnetic layer bridging between the first and second monitoring coils to provide inductive coupling therebetween;

a magnetic shaping layer deposited on top of the monitoring magnetic layer by a deposition C, the magnetic shaping layer covering the monitoring magnetic layer except for an exposed portion of the monitoring magnetic layer which corresponds to said selected portion of the monitored magnetic layer; and each of the first and second monitoring coils having first and second ends, the first and second ends of the first monitoring coil being connected to first and second pads respectively and the first and second ends of the second monitoring coil being connected to third and fourth pads respectively, whereby, in response to an alternating current conducted through the first monitoring coil via said first and second pads, an output due to said inductive coupling between the first and second monitoring coils is generated at the third and fourth pads for indicating said magnetic property of said selected portion of the monitored magnetic layer.

21. A combination as claimed in claim 20, wherein said magnetic property is permeability.

22. A combination as claimed in claim 21, wherein said deposition A is vacuum deposition.

23. A combination as claimed in claim 22, including:

said at least one monitoring system being replicated to provide a plurality of monitoring systems on said wafer; and each monitoring system having a different exposed portion which corresponds to a respective different selected portion of said monitored magnetic layer.

24. A combination as claimed in claim 23, including:

the monitored magnetic layer being a second pole piece of an inductive magnetic head which has front and back slopes with a yoke portion therebetween; and each monitoring magnetic layer being first and second replicated second pole pieces which are on top of first and second monitoring coil layers respectively.

25. A combination as claimed in claim 24, including:

the second pole piece being a component of a magnetic head which includes a first pole piece deposited by a deposition D, an insulation stack deposited by a plurality of depositions E, and at least one coil layer deposited by deposition B so that the coil layer is embedded in said insulation stack and the insulation stack is sandwiched between the first and second pole pieces; and each of the monitoring systems having first and second replicated first pole pieces deposited by said deposition D, first and second replicated insulation stacks deposited by deposition E so that the first and second monitoring coil layers are embedded in the first and second replicated insulation stacks and the first and second replicated insulation stacks are sandwiched between the first and second replicated pole pieces.

26. A combination as claimed in claim 25, wherein at least one of said selected portions is the back slope of the second pole piece.

27. A combination as claimed in claim 25, wherein at least one of said selected portions is the front slope of the second pole piece.

28. A combination as claimed in claim 25, wherein at least one of said selected portions is the yoke of the second pole piece.

29. A combination as claimed in claim 25, including:
a plurality of selected portions including the front and back slopes and the yoke of the second pole piece; and
one of the first and second replicated second pole pieces of each of the monitoring systems including a respective exposed portion which corresponds to a respective selected portion of said second pole piece.

30. A combination as claimed in claim 29, including:
one of the monitoring systems having its first and second replicated second pole pieces completely covered by a shaping layer deposited by deposition C without any exposed portions.

31. A combination as claimed in claim 29, including:
means connected to said first pair of pads for introducing said current into said first and second pads and means connected to said third and fourth pads for receiving an output from said third and fourth pads.

32. A combination as claimed in claim 29, including:
a magnetic shaping layer deposited by deposition C on top of at least said back slope and said yoke of said second pole piece.

33. A combination as claimed in claim 29, including:
a magnetic shaping layer deposited by deposition C on top of said front and back slopes and the yoke of said second pole piece.

34. A method for determining a magnetic property of at least one magnetic head at a wafer level, the method comprising:
depositing at least first, second and third substantially identical magnetic heads on a wafer with each magnetic head having a coil layer and a second pole piece;
joining the second pole pieces of the second and third magnetic heads so that the coil layers of the second and third magnetic head are magnetically coupled;
depositing a magnetic shaping layer on top of the second pole pieces of the second and third magnetic heads except for an exposed portion of the second pole piece of one of the second and third magnetic heads, the exposed portion corresponding to a selected portion of the second pole piece of the first magnetic head; and
conducting a current through the coil layer of the second magnetic head and receiving an output from the coil layer of the second magnetic head for indicating said magnetic property of the selected portion of the second pole piece of the first magnetic head.

35. A method as claimed in claim 34, including:
the second pole piece of each of the first, second and third magnetic heads having a front slope, a back slope and a yoke therebetween; and
exposing one of the front slope, back slope and the yoke of the second pole piece of one of the second and third magnetic heads corresponding to one of the front slope, back slope and the yoke of the second pole piece of the first magnetic head.

36. A method as claimed in claim 35, including:
a monitoring system which includes said second and third magnetic heads and the magnetic shaping layer;

replicating said monitoring system to provide a plurality of monitoring systems on said wafer; and
depositing the shaping layer in each of the monitoring systems to expose a different portion of one of the second pole pieces of the monitoring system which corresponds to a selected portion of the second pole piece of the first magnetic head.

37. A method as claimed in claim 35, including:
a monitoring system which includes said second and third magnetic heads and the magnetic shaping layer;
replicating said monitoring system to provide a plurality of monitoring systems on said wafer; and
omitting a portion of the magnetic shaping layer to expose a front slope of a second pole piece of a first one of the monitoring systems;
omitting a portion of the magnetic shaping layer to expose a back slope of a second pole piece of a second one of the monitoring systems; and
omitting a portion of the magnetic shaping layer to expose a yoke of a second pole piece of a third one of the monitoring systems.

38. An apparatus as claimed in claim 37, wherein said magnetic property is permeability.

39. A method of monitoring a magnetic property of a selected portion of a monitored magnetic layer, the method comprising the steps of:
providing a wafer;
depositing said monitored magnetic layer on the wafer by a deposition A;
fabricating at least one monitoring system on the wafer by:
depositing first and second monitoring coils on the wafer by a deposition B, with the first monitoring coil having first and second ends, and the second monitoring coil having first and second ends;
depositing a monitoring magnetic layer over the first and second monitoring coils respectively by said deposition A, the monitoring magnetic layer substantially replicating said monitored magnetic layer, the monitoring magnetic layer bridging between the first and second monitoring coils to provide inductive coupling therebetween;
depositing a magnetic shaping layer by a deposition C on top of the monitoring magnetic layer that covers the monitoring magnetic layer except for an exposed portion of the monitoring magnetic layer which corresponds to said selected portion of the monitored magnetic layer; and
connecting first and second pads to the first and second ends of the first monitoring coil and connecting third and fourth pads to the first and second ends of the second monitoring coil; and
conducting a current through the first monitoring coil via the first and second pads, and receiving an output at the third and fourth pads indicative of said magnetic property of said selected portion of the monitored magnetic layer.

40. A method as claimed in claim 39, wherein said magnetic property is permeability.

41. A method as claimed in claim 40, wherein said second deposition is vacuum deposition.

42. A method as claimed in claim 41, comprising the steps of:
depositing a plurality of monitoring systems on said wafer; and providing each monitoring system with a different exposed portion which corresponds to a respective selected portion of said monitored magnetic layer.

43. A method as claimed in claim 42, including:

the deposition of the monitored magnetic layer by deposition A forming a second pole piece of an inductive magnetic head which has front and back slopes with a yoke portion therebetween and the deposition of the monitoring magnetic layer by deposition A producing first and second replicated second pole pieces covering said first and second monitoring coil layers.

44. A method as claimed in claim 43, including:

depositing a first pole piece deposited by a deposition D, depositing an insulation stack deposited by a plurality of depositions E, and depositing at least one coil layer deposited by said deposition B so that the coil layer is embedded in said insulation stack and the insulation stack is sandwiched between the first and second pole pieces to form an inductive magnetic head; and for each of the monitoring systems, depositing first and second replicated first pole pieces deposited by said deposition D, depositing first and second replicated insulation stacks deposited by deposition E so that the first and second monitoring coil layers are embedded in the first and second replicated insulation stacks and the first and second replicated insulation stacks are sandwiched between the first and second replicated pole pieces.

45. A method as claimed in claim 44, wherein at least one of said selected portions is the back slope of the second pole piece.

46. A method as claimed in claim 44, wherein at least one of said selected portions is the front slope of the second pole piece.

47. A method as claimed in claim 44, wherein at least one of said selected portions is the yoke of the second pole piece.

48. A method as claimed in claim 44, including:

a plurality of selected portions including the front and back slopes and the yoke of the second pole piece; and one of the first and second replicated second pole pieces of each of at least some of the monitoring systems including an exposed portion which corresponds to a respective selected portion of said second pole piece.

49. A method as claimed in claim 48, including:

depositing a magnetic shaping layer by deposition C on top of said second pole piece so as to cover at least said back slope and said yoke.

50. A method as claimed in claim 48, including:

depositing the shaping layer by deposition C on the first and second replicated second pole pieces of one of the monitoring systems with no exposed portions.

* * * * *